United States Patent [19]

Tischler et al.

[11] Patent Number: 4,800,211
[45] Date of Patent: Jan. 24, 1989

[54] 5-METHYLTHIO-3-HYDROXYBENZO[B]THIOPHENE-2-CARBOXAMIDE DERIVATIVES AS CYCLOOXYGENASE AND LIPOXYGENASE INHIBITORS

[75] Inventors: Allan N. Tischler, Westfield; Philippe L. Durette, New Providence; Bruce E. Witzel, Westfield; Thomas J. Lanza, Jr., Edison, all of N.J.

[73] Assignee: Merck & Co., Inc., Rahway, N.J.

[21] Appl. No.: 897,576

[22] Filed: Aug. 18, 1986

[51] Int. Cl.[4] .................... A61K 31/38; C07D 333/70
[52] U.S. Cl. ...................................... 514/443; 549/54; 549/55
[58] Field of Search ..................... 549/55, 54; 514/443

[56] References Cited

U.S. PATENT DOCUMENTS 3,413,308 11/1968 Bockstahler .......................... 549/55

FOREIGN PATENT DOCUMENTS 2024220 1/1980 United Kingdom .................. 549/55

OTHER PUBLICATIONS

Shen et al, The Development of Antiasthma Drug, Part III, ed, D. R. Buckle et al, Butterworth Publishers, Kent England 1980, pp. 315, 317 and 331–335.

P. Gayral, et al., *Eur. J. Med. Chem.*, 20, 187–189 (1985).

*Primary Examiner*—Richard A. Schwartz
*Attorney, Agent, or Firm*—Joseph F. DiPrima; Michael C. Sudol; Mario A. Monaco

[57] ABSTRACT

3-Hydroxybenzo[b]thiophene-2-carboxamide derivatives have been prepared by:

(1) treating a substituted 2-halobenzoate with a thioacetamide.
(2) treating a substituted thiosalicylate with an appropriately substituted haloacetamide; and
(3) further synthetic modification of compounds prepared above.

These compounds have been found to be effective inhibitors of both cyclooxygenase and lipoxygenase and thereby useful in the treatment of pain, fever, inflammation, arthritic conditions, asthma, allergic disorders, skin diseases, cardiovascular disorders, psoriasis, inflammatory bowel disease, glaucoma or other prostaglandins and/or leukotriene mediated diseases.

6 Claims, No Drawings

5-METHYLTHIO-3-HYDROXYBENZO[B]THIOPHENE-2-CARBOXAMIDE DERIVATIVES AS CYCLOOXYGENASE AND LIPOXYGENASE INHIBITORS

BACKGROUND OF THE INVENTION

This invention relates to benzothiophenes, particularly, 3-hydroxybenzo[b]thiophene-2-carboxamides, which are found to be effective cyclooxygenase and 5-lipoxygenase inhibitors and are therefore useful in the treatment of inflammation and other prostaglandin and leukotriene mediated diseases. They are also found to be useful in the treatment of elevated intraocular pressure especially when accompanied by pathological damage.

Among various potent biological mediators derived from the oxygenation of arachidonic acid, prostaglandins and leukotrienes have been linked to various diseases. Notably, the biosynthesis of prostaglandins has been identified as a cause of inflammation, arthritic conditions (e.g., rheumatoid arthritis, osteoarthritis and gout), psoriasis, inflammatory bowel disease, and pain. Furthermore, the formation of leukotrienes has been connected to immediate hypersensitivity reactions and pro-inflammatory effects. It has been established that arachidonic acid undergoes oxygenation via two major enzymatic pathways:

(1) The pathway catalyzed by the enzyme cyclooxygenase; and
(2) The pathway catalyzed by the enzyme 5-lipoxygenase.

Interruption of these pathways by enzyme inhibition has been explored for effective therapy. For example, non-steroidal anti-inflammatory drugs (NSAID), such as, aspirin, indomethacin and diflunisal, are known cyclooxygenase inhibitors which inhibit the process wherein arachidonic acid is oxygenated via cyclooxygenase to prostaglandins and thromboxanes.

Recently, it has been observed that certain leukotrienes are responsible for diseases related to immediate hypersensitivity reactions, such as human asthma, allergic disorders, and skin diseases. In addition, certain leukotrienes and derivatives thereof are believed to play an important role in causing inflammation (B. Samuelsson, *Science*, 220, 568 (1983); D. Bailey et al, *Ann. Rpts. Med. Chem.*, 17, 203 (1982)).

Conditions involving elevated intraocular pressures which are too high for normal function may result in irreversible loss of visual function. For example, glaucoma, if untreated, may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many $\beta$-adrenergic blocking agents are effective in reducing intraocular pressure. While many of these agents are effective in reducing intraocular pressure, they also have other characteristics, e.g. membrane stabilizing activity, that are not acceptable for chronic ocular use.

To be an effective and acceptable topical agent, for treating inflammation in the eye, or ocular hypertension related diseases such as glaucoma, the drug must not only penetrate the ophthalmic tissues to reach the active sites within the eye, but it must also be devoid of those side effects including irritation, allergic reaction and the like which would militate against long term administration.

DETAILED DESCRIPTION OF THE INVENTION

A. Scope of the invention

The present invention relates to novel compounds of formula (I):

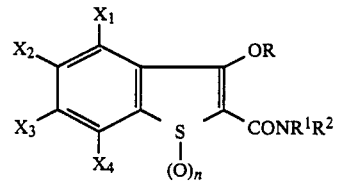

or a pharmaceutically acceptable salt thereof wherein R is
(a) H;
(b) loweralkyl, especially $C_{1-6}$ alkyl such as methyl, ethyl, i-propyl n-propyl, t-butyl, n-butyl, i-pentyl, n-pentyl and n-hexyl;
(c) aryl especially $C_{6-14}$ aryl e.g., naphthyl, anthryl, phenyl or substituted phenyl of formula

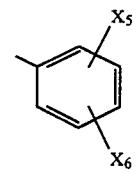

wherein $X_5$ and $X_6$ independently are:
(1) Q, where Q is H, loweralkyl especially $C_{1-6}$ alkyl, haloloweralkyl, especially fluoro or chloro $C_{1-6}$ alkyl such as trifluoromethyl, phenyl or substituted phenyl, or naphthyl;
(2) halo, such as chloro, fluoro, bromo or iodo;
(3) loweralkenyl, especially $C_{2-6}$ alkenyl such as ethenyl and allyl;
(4) loweralkynyl, especially $C_{2-6}$ alkynyl, for example, ethynyl or n-butynyl;
(5) —SQ;
(6) —OQ;
(7) —CHQCOQ$^1$, where Q$^1$ is Q and can be the same as or different from Q;
(8) —CHQCOOQ$^1$;
(10) —CH$_2$SQ or —CHQSQ$^1$;
(11) —CH$_2$OQ or —CHQOQ$^1$;
(12) —COQ;
(13) —COOQ;
(14) —OCOQ;
(15) —NQQ$^1$;
(16) —NQCOQ$^1$;
(17) —NQ(OQ$^1$);
(18) —NQ(SQ$^1$);
(19) —NQSO$_2$Q$^1$;
(20) —SO$_2$NQQ$^1$;
(21) —SOQ;
(22) —SO$_2$Q;
(23) —SO$_3$Q;
(24) —CN;

(25) —NO$_2$;
(26) —CONQQ$^1$;
(27) —NO;
(28) —CSQ;
(29) —CSNQQ$^1$;
(30) —CF$_2$SQ;
(31) —CF$_2$OQ;
(32) —NQCONHQ$^1$ or NQCONQ$^1$Q$^2$;
(d) lowercycloalkyl especially C$_{3-6}$ cycloalkyl, e.g., cyclopropyl, cyclopentyl and cyclohexyl;
(e) haloloweralkyl especially halo C$_{1-6}$ alkyl, e.g. CF$_3$—, CHF$_2$—, C$_2$F$_5$—;
(f) heteroaryl or heteroaryl substituted with X$_5$ and X$_6$ especially pyridyl, pyrryl, furyl or thienyl wherein X$_5$ and X$_6$ are as previously defined;
(g) benzyl or substituted benzyl of formula

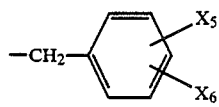

wherein X$_5$ and X$_6$ are as previously defined;
(h) loweralkynyl especially C$_{1-6}$ alkynyl such as —C≡CH; CH$_3$—C≡C—, or HC≡C—CH$_2$—;
(i) loweralkenyl especially C$_{1-6}$ alkenyl, such as CH$_2$=CH—, CH$_3$CH=CH—, CH$_2$=CHCH$_2$—, CH$_3$CH=CH—CH$_2$— or (CH$_3$)$_2$C=CH;
(j) phenylloweralkenyl of formula

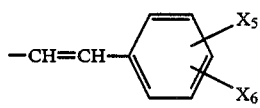

where X$_5$ and X$_6$ are as previously defined; or
(k) phenylloweralkynyl of formula

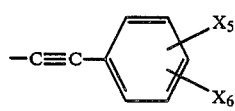

where X$_5$ and X$_6$ are as previously defined;
(l)

wherein R$^5$ is R;
(m)

(n)

wherein R$^6$ is R$^5$ and can be the same as or different from R$^5$;
(o)

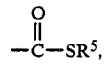

(p)

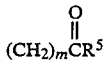

wherein m is 1 or 2;
(q) —(CH$_2$)$_m$OR$^5$;
(r)

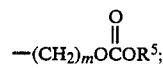

(s) —(CH$_2$)$_m$NR$^5$R$^6$; or
(t)

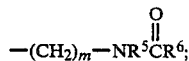

n is 0, 1 or 2;
X$_1$, X$_2$, X$_3$ and X$_4$ independently are
 (a) R as previously defined; or
 (b) X$_5$;
R$^1$ and R$^2$ independently are:
 (a) R except that when R is H or chlorine, R$^1$ and R$^2$ independently cannot be chlorophenyl, dichlorophenyl, trichlorophenyl or chloronitrophenyl; or
 (b) R$^1$ and R$^2$ may join together forming a ring of structure:

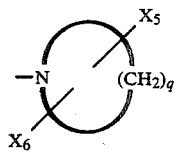

wherein q is 3–7; X$_5$ and X$_6$ are as previously defined.

Preferably, an enzyme inhibitor of this invention is of formula:

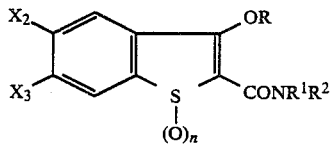

wherein X$_2$, X$_3$, R, R$^1$, R$^2$, and n are as previously defined.

More preferably, a dual enzyme inhibitor of this invention is formula:

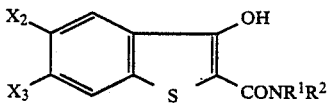

wherein X$_2$, X$_3$, R$^1$ and R$^2$ are as previously defined.

Even more preferably, a dual enzyme inhibitor of this invention is of formula:

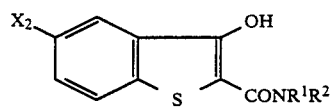

wherein
X₂ is as previously defined;
R¹ and R² independently are:
(a) hydrogen;
(b) loweralkyl;
(c) phenyl or substituted phenyl;
(d) heteroaryl or substituted heteroaryl, especially thienyl, furyl or pyrryl.

The representative compounds of the present invention are those listed in the following tables:

TABLE I

| $X_2$ | R | $R^1$ | $R^2$ | m.p. |
|---|---|---|---|---|
| H | H | H | -CH(CH₃)-phenyl | 142-144° |
| H | H | H | indanyl | 150-152° |
| CH₃S | H | H | -CH₂-phenyl | 159° |
| H | H | H | -CH₂-(CF₃-phenyl) | 139-141° |
| Cl | COCH₃ | H | CF₃-phenyl | 184-186° |
| Cl | COC(CH₃)₃ | H | CF₃-phenyl | 146-148° |
| CH₃ | COCH₃ | H | Cl-phenyl | 156-158° |
| CH₃ | COC(CH₃)₃ | H | Cl-phenyl | 129-131° |

TABLE I-continued

Structure: benzothiophene with $X_2$ on benzene ring, $OR$ at 3-position, and $C(=O)N(R^1)(R^2)$ at 2-position.

| $X_2$ | R | $R^1$ | $R^2$ | m.p. |
|---|---|---|---|---|
| Cl | $\overset{O}{\overset{\|}{C}}CH_2CH_2CO_2CH_2CH_3$ | H | 3-CF$_3$-phenyl | 145–147° |
| CH$_3$ | $\overset{O}{\overset{\|}{C}}CH_2CH_2CO_2CH_2CH_3$ | H | 3-Cl-phenyl | 118–120° |
| H | H | H | benzyl (CH$_2$-phenyl) | 123.5° |
| CH$_3$S | $\overset{O}{\overset{\|}{C}}CH_2CH_2CO_2CH_2CH_3$ | H | benzyl (CH$_2$-phenyl) | 125–127° |
| Cl | H | H | benzyl (CH$_2$-phenyl) | 175–177° |
| H | $\overset{O}{\overset{\|}{C}}CH_3$ | H | 3-Cl-phenyl | 149° |
| H | H | CH$_3$ | phenyl | 111° |
| Cl | $\overset{O}{\overset{\|}{C}}CH_3$ | H | 3-Cl-phenyl | 159–161° |
| Cl | H | CH$_3$ | phenyl | 182–184°(dec) |
| Cl | H | H | 4-Cl-phenyl | 237–239°(dec) |
| Cl | H | H | 3-CF$_3$-phenyl | 193–195°(dec) |

TABLE I-continued

Structure: benzothiophene with $X_2$ on benzene ring, OR at 3-position, and $-C(=O)-NR^1R^2$ at 2-position.

| $X_2$ | R | $R^1$ | $R^2$ | m.p. |
|---|---|---|---|---|
| Cl | H | H | 3-(COOH)-phenyl | 302°(dec) |
| $NO_2$ | H | H | 3-Cl-phenyl | 242°(dec) |
| $NH_2$ | H | H | 3-Cl-phenyl | 220°(dec) |
| $CO_2CH_3$ | H | H | 3-Cl-phenyl | 196–198°(dec) |
| Cl | H | H | 3-($COCH_3$)-phenyl | 250–252°(dec) |
| $CH_3S$ | H | H | 3-Cl-phenyl | 156–157° |
| Cl | H | H | $-CH_2-$(3-Cl-phenyl) | 184–186° |
| Cl | H | $CH_3$ | 3-Cl-phenyl | 181° |
| Cl | H | H | $-CH_2-$(3-OH, 4-I, 5-$C(CH_3)_3$-phenyl) | 160–162° |
| Cl | H | $CH_3$ | $-CH_2-$phenyl | 119–121° |

TABLE I-continued

[Structure: X₂-substituted benzothiophene with OR group and C(=O)N(R¹)(R²) group]

| X₂ | R | R¹ | R² | m.p. |
|---|---|---|---|---|
| Cl | H | H | 4-(COCH₃)phenyl | 257–259°(dec) |
| 2,4-difluorophenyl | H | H | 3-chlorophenyl | 210°(dec) |
| CH₃ | COCH₃ | H | 4-C(CH₃)₃phenyl | 172–174° |
| CH₃ | CCH₂CH₂CO₂CH₂CH₃ (O=) | H | 4-C(CH₃)₃phenyl | 93–95° |
| CH₃ | CC(CH₃)₃ (O=) | H | 4-C(CH₃)₃phenyl | 184–186° |
| H | H | H | phenyl | 232–234°(dec) |
| H | H | H | CH₂—C(=CH₂)—phenyl | 150–152° |
| H | H | H | CH₂CH(φ)(φ)  φ = phenyl | 152–154° |
| H | H | H | CH₂CH₂-phenyl | 131–133° |
| H | H | H | 3-(CF₃)phenyl | 205–208°(dec) |
| H | H | H | CH₂CH₂CH₂-phenyl | 116–118° |

TABLE I-continued

[Structure: benzothiophene with X₂ substituent, OR group, and C(=O)N(R¹)(R²) amide]

| X₂ | R | R¹ | R² | m.p. |
|---|---|---|---|---|
| H | H | H | CH₂CH₂-(N-methylpyrrol-2-yl) | 137–140° |
| H | H | H | -C₆H₄-CO₂CH₃ | 234–235° |
| H | H | H | CH(φ)(φ) (i.e., CH with two phenyl groups) | 155–163° |
| H | H | H | CH₂-C(CH₃)=CH₂ | 111–113° |
| H | H | H | CH₂-(furan-2-yl) | 115–116.5° |
| H | H | H | CH₂-(tetrahydrofuran-2-yl) | 88–91° |
| H | H | H | CH₂CH₂-C₆H₄-Cl | 150–154° |
| H | H | H | 2-fluorophenyl | 213–215° |

B. Preparation of the compounds of the invention

The compounds of the present invention are prepared from known starting materials via various procedures, for example, methods as described below:

Method A

By this method, an appropriately substituted thiosalicylate is reacted with a haloacetamide to give the ring closure product:

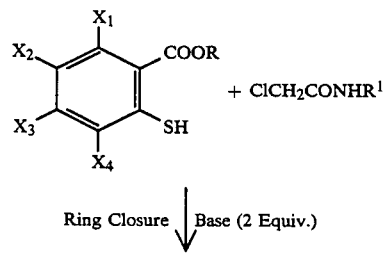

-continued

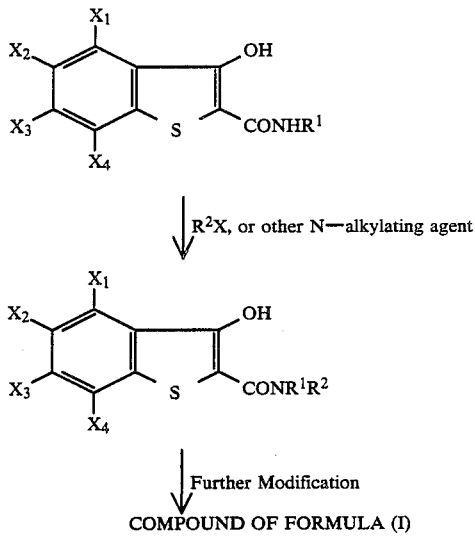

↓ R²X, or other N—alkylating agent

↓ Further Modification

COMPOUND OF FORMULA (I)

wherein the base is a strong base, for example, lithium diisopropylamide, NaOCH$_3$, LiO(n-Bu), NaOt-Bu, KOCH$_3$, etc; and the alkylation agent can be R²X, wherein X is halogen or sulfonate, such as OSO$_2$CF$_3$, OSO$_2$C$_6$H$_5$ or OSO$_2$CH$_3$.

Method B

A convenient method for preparing a 3-hydroxybenzo[b]thiophene-2-carboxamide, is described in the following scheme:

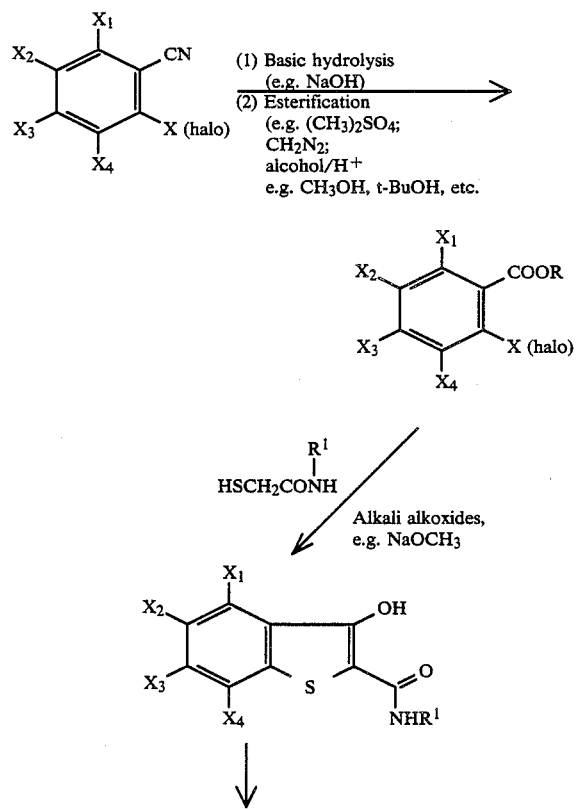

*Further modification to give compound of Formula (I).

Method (C)

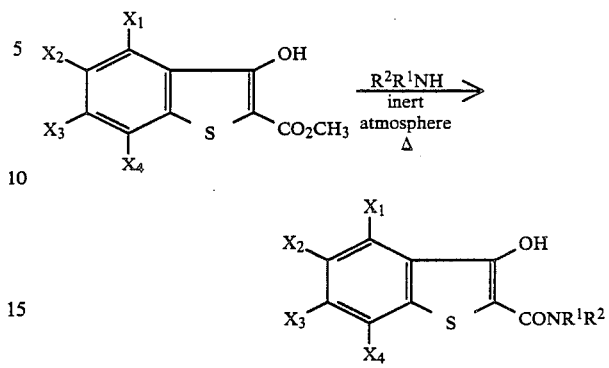

The pharmaceutically acceptable salts of compounds of Formula I (at the 3-hydroxy site when R is H) are readily prepared by conventional procedures well-known in the art. For example, a compound of Formula I is treated with an appropriate amount of a base, such as an alkali or alkaline earth metal hydroxide, e.g. sodium hydroxide, potassium hydroxide, and calcium hydroxide or an organic base such as an alkoxide, e.g., CH$_3$ONa, t-BuOK, or the like.

The pharmaceutically acceptable esters of the phenol of formula (I) can also be prepared by conventional methods. For example, (1) a compound of Formula (I) is treated with an acyl halide such as acetyl chloride or an acid anhydride such as acetic anhydride.

C. Utility of the compounds within the scope of the invention

This invention also relates to a method of treatment for patients (or mammalian animals raised in the dairy, meat, or fur industries or as pets) suffering from disorders or diseases mediated by prostaglandins and/or leukotrienes, and gastric irritation or lesion. More specifically, this invention is directed to a method of treatment involving the administration of one or more of the dual enzyme inhibitors of formula (I) as the active constituent.

Accordingly, a compound of Formula (I) can be used among other things to reduce pain and inflammation, to correct respiratory, cardiovascular, and intravascular alterations or disorders, and to regulate immediate hypersensitivity reactions that cause human asthma and allergic conditions.

For the treatment of inflammation, arthritis conditions, cardiovascular disorder, allergy, psoriasis, asthma, or other diseases mediated by prostaglandins and/or leukotrienes, a compound of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intravascular injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid. Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed.

Dosage levels of the order of from about 0.01 mg to about 150 mg per kilogram of body weight per day are useful in the treatment of the above-indicated conditions (about 0.5 mg to about 7.5 gms. per patient per day). For example, inflammation may be effectively treated by the administration of from about 0.2 to 50 mg of the compound per kilogram of body weight per day (about 20 mg to about 3.5 gms per patient per day). Preferably a dosage of from about 1 mg to about 20 mg per kilogram of body weight per day may produce good results (about 25 mg to about 1 gm per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

For use in treatment of ophthalmic conditions including those associated with elevated intraocular pressure such as glaucoma or other inflammation in the eye. The active compound can be administered topically or systemically when it is appropriate. The dose administered can be from as little as 0.1 to 25 mg or more per day, singly, or preferably on a 2 to 4 dose per day regimen although a single dose per day is satisfactory.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

When given by the topical route, the active drug or an ophthalmologically acceptable salt thereof such as the sodium or potassium salt is formulated into an ophthalmic preparation. In such formulations, from 0.1% to 15% by weight can be employed. The objective is to administer a dose of from 0.1 to 10 mg per eye per day to the patient, with treatment continuing so long as the condition persists.

Thus, in an ophthalmic solution, insert, ointment or suspension for topical delivery, or a tablet, intramuscular, or intravenous composition for systemic delivery, the active medicament or an equivalent amount of a salt thereof is employed, the remainder being carrier, excipients, preservatives and the like as are customarily used in such compositions.

As with all medications, dosage requirements are variable and must be individualized on the basis of the disease and the response of the patient.

D. Biological Data Supporting the Utility of the Compounds Within the Scope of the Invention.

The following is a summary of biological data from three bioassays. These data serve to illustrate that the compounds of formula (I) are dual cyclooxygenase/-lipoxygenase inhibitors useful as antiinflammatory, analgesic and antipyretic agents.

1. Platelet Activating Factor-Induced Hyperalgesia in the Rat.

In this assay, which is sensitive to inhibition by lipoxygenase inhibitors, but not cyclooxygenase inhibitors, compounds of formula (I) reduced the pain response to PAF (Table 1). Indomethacin, ibuprofen, piroxicam, and benoxaprofen were completely ineffective in this assay (Table 2).

Groups of 10 female Sprague-Dawley rats, 35–50 g (Taconic Farms), were fasted overnight prior to testing. Hyperalgesia was induced in the rat by the subplantar injection of 1 ug PAF in physiological saline. Pain threshold was measured by applying pressure to the plantar surface of the hindpaw by means of a compressed air driven piston with a 2 mm tip. Vocalization thresholds were obtained 3 hr after injection of the PAF. Compounds, prepared at various doses in 1% methylcellulose suspension, were administered perorally 30 min before PAF. For each drug treatment group, animals with response pressures in the inflamed paw of 200% of control was considered to be analgesic. The mean vocalization threshold for each group was also calculated.

TABLE 1

Effect of Compounds A and B on PAF-Induced Hyperalgesia in the Rat

| Treatment | Dose (mg/kg p.o.)[a] | % Analgesia[b] |
|---|---|---|
| Compound A[c] | 30 | 90 |
| Compound B[d] | 30 | 80 |

[a]Drug administered 30 min before PAF.
[b]Percentage of animals with vocalization threshold greater than 200% of vehicle-treated controls. Readings taken 3 hours after PAF.
[c]Compound A: N—(3-chlorophenyl)-3-hydroxy-5-(methylthio)benzo[b]thiophene-2-carboxamide.
[d]Compound B: 3-Hydroxy-5-(methylthio)-N—(phenyl-methyl)benzo[b]thiophene-2-carboxamide.

TABLE 2

Effect of Compound A and Standard Cyclcooxygenase Inhibitors in the PAF-induced Hyperalgesia Assay in the Rat

| Test Substance | Dose mg/kg p.o. | % Rats Exhibiting Analgesia |
|---|---|---|
| Compound A | 30 | 90 |
| Indomethacin | 10 | 10 |
| Piroxicam | 30 | 0 |
| Ibuprofen | 30 | 10 |
| Sulindac | 30 | 10 |
| Diflunisal | 30 | 10 |
| Aspirin | 100 | 10 |
| Naproxen | 30 | 10 |
| Benoxaprofen | 30 | 10 |

2. Inhibition of RBL-1 Cell 5-Lipoxygenase

The ability of the compound of Formula I, e.g., Compound A, to inhibit leukotriene biosynthesis was also measured in vitro against the RBL-1 cell 5-lipoxygenase. The protocol for measuring inhibition of 5-HETE formation has been published in R. W. Egan et al., "Advances in Prostaglandin, Thromboxane, and leukotriene Research", Vol. 11 (edited by B. Samuelsson et al., Raven Press, N.Y., 1983), p. 151. Results are given in Table 3.

TABLE 3

| Inhibition of RBL-1 Cell 5-Lipoxygenase | |
|---|---|
| Compound | Percent Inhibition |
| A | 83 (10 ug/ml) |
| | 74 (2 ug/ml) |
| | 58 (1 ug/ml) |
| | 48 (0.5 ug/ml) |

3. Inhibition of Cyclooxygenase

The dual enzyme inhibitory property of the compounds of formula I, e.g., compound A, was demonstrated by their ability to also inhibit microsomal ram vesicular gland cyclooxygenase. The protocol for measuring inhibition of this prostaglandin-producing enzyme has been published. Results are given in Table 4.

TABLE 4

| Inhibition of Microsomal Ram Vesicular Gland Cyclooxygenase | |
|---|---|
| Compound | Percent Inhibition |
| A | 95 (16.5 uM) |

EXAMPLE 1

3-Hydroxy-5-chloro-N-[(3-chlorophenyl)methyl]benzo[b]thiophene-2-carboxamide

To a solution of methyl 5-chloro-2-mercaptobenzoate (1.02 g; 0.005M) in 20 ml of methanol is added solid sodium methoxide (0.81 g; 0.015M; 3 eqv.) followed by N-[(3-chlorophenyl)methyl]chloroacetamide (1.10 g; 0.005M) and the mixture is refluxed under a nitrogen atmosphere for 30 minutes. The mixture is cooled to room temperature and added to a solution of 1.25 ml of glacial acetic acid in 20 ml of water and cooled to 0° C. The white solid is collected, washed with 50% methanol-water and air dried to give 1.60 g (91% yield) of the title compound; m.p. 184°–186° C.

EXAMPLE 2

3-Hydroxy-N-[(3-trifluoromethylphenyl)methyl]benzo[b]thiophene-2-carboxamide

To a solution of methyl thiosalicylate (0.67 g; 0.004M) in 20 ml of methanol is added solid sodium methoxide (0.65 g; 0.012M; 3 eqv.) followed by N-[(3-trifluoromethylphenyl)methyl]-chloroacetamide (1.0 g; 0.004M) and the mixture is refluxed under a nitrogen atmosphere for 30 minutes. The mixture is cooled to room temperature and added to a solution of 1.5 ml of glacial acetic acid in 25 ml of water and cooled to 0° C. The cream colored solid is collected, washed with 50% methanol-water, air dried, and recrystallized from nitromethane to give 1.05 g (78% yield) of the title compound; m.p. 139°–141° C.

EXAMPLE 3

3-Hydroxy-5-methoxycarbonyl-N-(3-chlorophenyl)-benzo[b]thiophene-2-carboxamide

Solid sodium methoxide (1.62 g; 0.030M; 3 eqv.) is added to a stirred mixture of methyl 2-bromo-5-methoxycarbonylbenzoate (2.74 g; 0.010M) and N-(3-chlorophenyl)thioacetamide (4.04 g; 0.020M) in 25 ml of methanol under a nitrogen atmosphere and the mixture is refluxed for 1.5 hour. The room temperature mixture is added to a solution of 3 ml of glacial acetic acid in 50 ml of water and cooled to 0° C. The cream colored solid is collected, washed with 50% methanol-water, air dried, and recrystallized from absolute ethanol to give the title compound as 2.43 g of fine white crystals (67% yield); m.p. 200°–202° C.

EXAMPLE 4

3-Hydroxy-5-nitro-N-(3-chlorophenyl)-benzo[b]thiophene-2-carboxamide

Solid sodium methoxide (1.94 g; 0.036M; 3 eqv.) is added to a stirred mixture of methyl 2-chloro-5-nitrobenzoate (2.59 g; 0.0120M) and N-(3-chlorophenyl)thioacetamide (2.42 g; 0.0120M) in 50 ml of methanol under a nitrogen atmosphere and the dark red mixture is refluxed for 10 minutes. The room temperature mixture is added to a solution of 3 ml of glacial acetic acid in 50 ml of water and cooled to 0° C. The yellow precipitate formed is collected, washed with 50% methanol-water, and dried under vacuum to give 4.02 g (96%) of the title compound. Rf=0.33 in TLC (Et$_2$O:hexane:AcOH; 1:1:1%).

EXAMPLE 5

3-Hydroxy-5-chloro-N-(3-chlorophenyl)benzo[b]thiophene-2-carboxamide

A mixture of methyl 3-hydroxy-5-chlorobenzo[b]thiophene-2-carboxylate (1.21 g; 0.005M) and 3-chloroaniline (1.28 g; 0.010M) is heated under a nitrogen atmosphere at 170° C. for 90 minutes. The reaction mixture was cooled to room temperature, taken up in 10 ml of ether, collected the solid, washed with 10 ml of ether, air dried, and recrystallized from ethyl acetate to give 0.95 g (56% yield) of the title compound as a light grey solid, m.p. 233°–235° C. (dec).

EXAMPLE 6

3-Hydroxy-N-(3-trifluoromethylphenyl)-benzo[b]thiophene-2-carboxamide

A mixture of methyl 3-hydroxy-benzothiophene2-carboxylate (1.04 g; 0.005M) and 3-trifluoromethylaniline (1.61 g; 0.010M) is heated under a nitrogen atmosphere at 170° C. for 90 minutes. and then at 200° C. for 30 minutes. The reaction was cooled at room temperature, taken up in ether and the solid was collected, washed with ether and air dried. The solid was recrystallized from ethyl acetate to give 0.96 g (57% yield) of the title compound; m.p. 205°–208° C. (dec).

What is claimed is:

1. The compound which is N-(3-chlorophenyl)-3-hydroxy-5-methylthiobenzo[b]thiophene-2-carboxamide or a pharmaceutically acceptable salt thereof.

2. A pharmaceutical composition for treating a disease selected from the group consisting of arthritic conditions and immediate hypersensitivity reaction comprising a pharmaceutically acceptable carrier and a non-toxic effective amount of compound according to claim 1.

3. A method of treating a disease selected from the group consisting of arthritic conditions and immediate hypersensitivity reaction comprising the administration to a subject in need of such treatment a non-toxic effective amount of compound according to claim 1.

4. The compound which is 3-hydroxy-5-methylthio-N-(phenylmethyl)benzo[b]thiophene-2- carboxamide or a pharmaceutically acceptable salt thereof.

5. A pharmaceutical composition for treating a disease selected from the group consisting of arthritic conditions and immediate hypersensitivity reaction comprising a pharmaceutically acceptable carrier and a non-toxic effective amount of compound according to claim 4.

6. A method of treating a disease selected from the group consisting of arthritic conditions and immediate hypersensitivity reaction comprising the administration to a subject in need of such treatment a non-toxic effective amount of compound according to claim 4.

* * * * *